| United States Patent [19] | [11] | 4,100,293 |
|---|---|---|
| Walser | [45] | Jul. 11, 1978 |

[54] TREATMENT OF HEPATIC DISORDERS WITH THERAPEUTIC COMPOSITIONS COMPRISING KETO ANALOGS OF ESSENTIAL AMINO ACIDS

[75] Inventor: Mackenzie Walser, Ruxton, Md.

[73] Assignee: The Johns Hopkins University, Baltimore, Md.

[21] Appl. No.: 669,589

[22] Filed: Mar. 23, 1976

Related U.S. Application Data

[63] Continuation-in-part of Ser. No. 461,222, Apr. 15, 1974, abandoned, which is a continuation-in-part of Ser. No. 355,327, Apr. 30, 1973, abandoned, which is a continuation-in-part of Ser. No. 270,986, Jul. 12, 1972, abandoned.

[51] Int. Cl.$^2$ .................... A61K 31/40; A61K 31/19; A61K 31/195
[52] U.S. Cl. .................... 424/274; 424/317; 424/319
[58] Field of Search .................... 424/317, 319, 274

[56] References Cited

U.S. PATENT DOCUMENTS

| 2,457,820 | 1/1949 | Howe et al. ..................... 424/319 |
| 3,764,703 | 10/1973 | Bergström et al. ................. 424/319 |

OTHER PUBLICATIONS

Chemical Abstracts 81:54452q (1974).
Chemical Abstracts 82:144958j (1975).
Richards et al., Lancet pp. 128–134 (Jul. 17, 1971), pp. 845–849 (Oct. 21, 1967).
Rudman, J. of Clincial Invest. 50, pp. 90–96 (1971).

*Primary Examiner*—Leonard Schenkman
*Attorney, Agent, or Firm*—Seidel, Gonda & Goldhammer

[57] ABSTRACT

Treatment of hepatic disorders, such as are characterized by hyperammonemia and portal-systemic encephalopathy, is advocated using compositions comprising keto analogs of certain essential amino acids. In the preferred embodiments, such compositions comprise the keto analogs of valine, phenylalanine, methionine, leucine and isoleucine.

25 Claims, No Drawings

TREATMENT OF HEPATIC DISORDERS WITH THERAPEUTIC COMPOSITIONS COMPRISING KETO ANALOGS OF ESSENTIAL AMINO ACIDS

STATEMENT OF GOVERNMENT INTEREST

The invention described herein was made in the course of work under a grant or award from the Department of Health, Education and Welfare.

CROSS-REFERENCE TO RELATED APPLICATIONS

This application is a continuation-in-part of U.S. application Ser. No. 461,222 (now abandoned) entitled "Composition and Method for Promotion of Protein synthesis and Suppression of Urea Formation in the Body", filed Apr. 15, 1974; which application Ser. No. 461,222 is a continuation-in-part of U.S. patent application Ser. No. 355,327 (now abandoned) having the same title and was filed Apr. 30, 1973 as a continuation-in-part of U.S. patent application Ser. No. 270,986 (now abandoned) entitled "Composition and Method of Treating Uremia" filed July 12, 1972.

The treatment of renal diseases with similar or related compositions is described in companion application Ser. No. 669,590 titled: "Promotion of Protein Synthesis and Suppression of Urea Formation in the Body by Keto Analogs of Essential Amino Acids", filed of even date herewith.

BACKGROUND OF THE INVENTION

A. Field of the Invention

The invention relates generally to therapeutic compositions for administration to humans suffering from hepatic disorders. The described compositions in the several embodiments thereof utilize keto analogs of certain essential amino acids administered orally or parenterally, which are effective in reducing the content of ammonia in the blood stream, thereby affording symptomatic relief and reducing the toxic effects of ammonia in the circulation.

B. Description of the Prior Art

It has heretofore been proposed to employ mixtures of the essential amino acids in the treatment of uremic conditions (Bergstrom et al., U.S. Pat. No. 3,764,703). Other workers have suggested possible substitution of the corresponding keto analogs of one or more of such essential amino acids in treatment of uremic disorders, based on the assumption that such keto analogs might combine with nitrogen derived from urea breakdown in the intestines. It has subsequently been demonstrated that these assumptions were not valid. The successful treatment of renal disorders by particular compositions comprising keto analogs of certain of the essential amino acids has, however, been reported in the literature by the present applicant; see Walser, M. et al., 1973, "The Effect of Keto-analogues of Essential Amino Acids in Severe Chronic Uremia", *Journal of Clinical Investigation,* 52:678.

Prior to the work undertaken by the present applicant, there has been no reported clinical investigation of the use of keto analogs of amino acids in the treatment of hepatic disorders. (A footnote in the *J. Clin. Invest.,* 50:90, speculates, without supporting data, on a potential possible application of a protein-free diet containing unnamed keto acid analogs, in the treatment of hepatic patients with ammonia intoxication, provided efficient amination or trans-amination of the keto acids could be performed in the diseased liver and/or extrahepatic tissues of these subjects). Prior art treatment of hepatic failure, such as is characterized by hyperammonemia and portal systemic encephalopathy, is generally based on attempts to reduce the production of ammonia in the intestines and to restrict dietary protein. Antibiotics are usually applied to prevent urea breakdown.

The previous attempts to reduce intestinal ammonia release in the treatment of hepatic disorders are based on the belief that the high peripheral blood ammonia present in these conditions is responsible for the symptoms of these disorders.

SUMMARY OF THE INVENTION

Contrary to prior teachings, it has been found in experiments leading to the present invention, that urea breakdown is not necessary for the amination of keto acids in the body tissue. Such amination, in fact, occurs in muscle tissue. The total effect of the amination process is the reduction in the accumulation of urea precursors in the body. By the present invention, the production of ammonia in the bloodstream is reduced while desired protein synthesis is simultaneously promoted. Exogenous protein requirements are also minimized by diverting nitrogen precursors in the body away from urea formation (urea is excreted, resulting in bodily nitrogen loss) by combination of these precursors with the administered keto acid analogs of essential amino acids to form the desired amino acids. These endogenous amino acids are thus more efficiently reutilized in the hereinafter described treatment of hepatic disorders.

By administration of the compositions of the present invention comprising the keto analogs of certain essential amino acids, the nitrogen-containing urea precursors, such as ammonia, combine with the keto acid analogs. Also the nitrogen-loss mechanisms in the body are altered. Thus, the desired essential amino acids are formed by synthesis through reaction of the keto acid analogs with ammonia in normal muscle tissue and in the reduction of ammonia content in the blood stream, both being desirable objectives in the treatment of hepatic disorders. In hepatic disorders, the liver may be incapable of performing its usual metabolic function. By the above described synthesis of the essential amino acids in normal muscle tissue, the impaired liver function is surmounted. According to the present invention, a positive nitrogen balance can be achieved by oral or parenteral administration of the described keto acids, with reduced nitrogen wastage from the body.

DESCRIPTION OF THE PREFERRED EMBODIMENTS

The particular embodiments of the composition employed in practice of the present invention utilize keto analogs of at least five of the essential amino acids. These comprise the keto analogs of valine, methionine, leucine, isoleucine and phenylalanine, in acid or salt form. The administered compositions further comprise at least three other essential amino acids: lysine, threonine and tryptophan, which may be supplied as the levo-rotary isomers of such acids or optionally any one or more of these in the form of the alpha-keto acid analog or as a salt of such analog. The compositions preferably also comprise L-arginine, which is deemed beneficial in hepatic disorders because it tends to bring about a reduction of blood ammonia. Moreover, arginine is also useful in treatment of children with congenital urea-cycle enzyme defects who are incapable of synthesizing arginine. While it was earlier recognized that histidine was essential in renal disorders, only recently has it been recognized as possibly essential in all humans. Accordingly, both L-arginine and L-histidine may be included in the present compositions administered in the treatment of hepatic disorders. In patients receiving some dietary protein, histidine may be omitted from the administered composition, since adequate histidine may be provided by such ingested protein.

The described compositions may be given orally as a mixture in salt-free boullion or in gelatin capsules, or parenterally in aqueous solution, the keto analogs being preferably in the form of their sodium or calcium salts, while the other components are in levo form of their free amino acids, particularly as L-lysine, L-threonine and L-arginine. For individuals having a tendency to retain sodium, use of the calcium salt is advocated.

The keto acid analogs of the described amino acids are listed in Table I below:

Table I

| Amino Acid | Keto-Acid Analog |
|---|---|
| Valine | Alpha-ketoisovaleric acid |
| Phenylalanine | Phenylpyruvic acid |
| Methionine | Alpha-keto-gamma-methylthiobutryic acid |
| Leucine | Alpha-ketoisocaproic acid |
| Isoleucine | Alpha-keto-beta-methylvaleric acid |
| Histidine | Imidazolepyruvic acid |
| Tryptophan | Indolepyruvic acid |
| Lysine | Alpha-keto-gamma-aminocaproic acid |
| Threonine | Alpha-keto-beta-hydroxybutyric acid |
| Arginine | Alpha-keto-gamma guanido valeric acid |

The keto-acid analog of isoleucine exists in two optical isomeric forms, these two forms of the keto-acid analog of isoleucine are interconverted in the body. The keto analogue of L-isoleucine, the naturally occurring amino acid, is dextrorotary. When administered, it is racemized in the body. Since the racemic composition of the keto analogues of L-isoleucine is considerably less expensive than the pure dextro form and has been found equally effective for the purposes of the present invention, the use of racemic alpha-keto-beta-methyl-valeric acid has pronounced ecomonic advantages.

The keto-acid analogs of the first five listed amino acids of Table I are most readily available at reasonable costs. Accordingly, the amino acids themselves of the last five listed amino acids may be used in the several embodiments of the present composition of matter. The keto-acid analogs of histidine and tryptophan are more readily available than are the keto-acid analogs of lysine and threonine, and may thus also be more commonly used in practice of the invention.

While histidine and arginine are regarded as essential amino acids based on their dietary requirement for growth of rats, these were not generally considered as essential in humans. More recent investigations, however, indicated that histidine might well be essential in treatment of uremic patients on restricted protein intake and possibly might be an essential amino acid in all human subjects, contrary to earlier beliefs. Accordingly, L-histidine or its keto analog is preferably included as a component in the compositions of the present invention.

In order to understand the activity of the invention in the body, careful tests on rats were conducted. It was found that isolated livers of rats perfused with 2 to 5 mM of alpha-keto isovaleric acid, alpha-keto-beta-methylvaleric acid, phenylpyruvic acid, alpha-keto-gamma-methylthiobutyric acid, or alpha-keto isocaproic acid, utilize all five compounds rapidly at the rate of 1 to 4 micro mols per minute. Glucose release and urea production were unaffected. However, there was a marked increased in release of the corresponding amino acids. Approximately 25% of the keto-acid analogs of leucine, methionine, and phenylalanine; approximately 8% of the keto-acid analog of isoleucine; and approximately 8% of the keto acid analog of valine taken up reappeared as amino acid. Levels of critical metabolites in freeze-clamped liver were unaffected.

The keto-acid analogs of phenylalanine, valine, and isoleucine were also tested in perfused hind quarters at 2 and 8 mM. All were rapidly utilized at a rate of 2 to 4 micro mols per minute per 30 grams of muscle. The corresponding amino acids appeared in the medium in greatly increased quantities. Alanine release diminished. Thus, these five keto-acids are rapidly converted to amino acids both in rat liver and muscle both when these compounds are administered singly and when five of them are given simultaneously. Degradation also occurs and particularly to a larger extent in the keto-acid analogs of the branched chain amino acids: valine, leucine and isoleucine. Treatment with the present composition of matter has not caused keto-acids to accumulate in the blood.

As indicated above, the administered optically active keto analog of isoleucine is rapidly racemized in the body. Whether so administered as the optically active isomer or directly in racemic form, a portion thereof accumulates as alloisoleucine. It has not been established whether the L-alloisoleucine thus appearing in the blood stream serves a useful purpose. Applicant has established, however, that the alloisoleucine is not toxic, contrary to possible expectations, and furthermore that it is not incorporated into protein. This partial conversion of the administered keto analogue of isoleucine to alloisoleucine in addition to the desired isoleucine further supports the rationale for inclusion of increased quantities of the keto analog of isoleucine in the preferred compositions of the present invention. It has been established by work carried out in development of the present invention not only that desired nitrogen balance can be maintained when using the racemic keto analogue of isoleucine but also that its use in the described compositions is safe and effective in long term therapy.

Treatment of Hepatic Disorders In Adults

Hepatic disorders, such as are characterized by hyperammonemia and portal-systemic encephalopathy, have previously been treated by attempts to reduce intestinal ammonia release, since the high peripheral blood ammonia present in these conditions is believed responsible for the symptoms of the disorders. Protein restriction is commonly required, also. Usual treatment consists of reducing the bacterial flora of the intestine by oral administration of poorly absorbed antibiotics, such as neomycin. The disorder known as portal-systemic encephalopathy, a condition in which the portal circulation draining the intestines abnormally communicates with the systemic circulation, results in passage of ammonia into the systemic circulation with resulting changes in cerebral and nervous function.

Thus, ammonia accumulates in the blood rather than being converted to urea in the liver as would normally occur. Individuals suffering from this disorder have defective liver functions and cannot tolerate protein. Again, prior treatment centers on attempts to reduce the production of ammonia in the intestines by means of antibiotics, lactulose, or cathartics. Although it is now believed that these individuals generally suffer from protein deficiencies, the administration of amino acids has been contraindicated due to the extra load of ammonia produced by the eventual breakdown of the amino acids.

The present invention provides an effective treatment for these hepatic disorders by promoting utilization of the circulating ammonia in protein synthesis, thereby leading to a partial correction in protein deficiency. Also, the body's mechanisms for producing urea are altered and thus conserve protein. Thus, blood ammonia is reduced with resulting symptomatic relief by virtue not only of the combination of nitrogen-containing urea precursors, such as ammonia, with the keto-acid analogs of amino acids but also due to the alteration of the body's mechanisms for conserving protein. Essential amino acids are formed which tend to correct the nutritional disturbance while reducing the toxic effects of ammonia within the circulation.

In Table II below, a practical range of the individual components of the mixture is set out, intended for administration to adult hepatic patients of below average body weight (less than 50 kgs.) at the lower end of the disclosed range and to patients of above average body weight (above about 75 kgs.) at the upper end of the disclosed range. When individual idiosyncrasies are encountered, such as abnormal balance of the corresponding amino acids in the patient's s blood, the dosage of the individual components of the administered mixture can be modified. In particular, tryptophan and the analogs of phenylalanine and methionine may be omitted owing to an excess of these amino acids in certain patients.

Table II

| Quantity | Substance |
| --- | --- |
| 0.0 – 3.0 grams | phenylpyruvic acid; sodium salt |
| 4.0 – 8.0 grams | alpha-ketoisovaleric acid; sodium salt |
| 3.0 – 5.0 grams | alpha ketoisocaproic acid; sodium salt |
| 0.0 – 3.0 grams | alpha-keto-gamma-methylthiobutyric acid; sodium salt |
| 2.0 – 4.0 grams | alpha-keto-beta-methylvaleric acid; sodium salt |
| ~0 – 0.1 gram | L-tryptophan |
| ~0 – 0.4 gram | L-threonine |
| ~0 – 0.4 gram | L-lysine monohydrochloride |
| 1.0 – 4.0 grams | L-arginine |

The small amount of protein included in the patient's regular diet may furnish the needed amount of histidine. If analysis of the patient's s blood after administration of the mixture set out in Table II indicates that insufficient histidine is present, the composition may be modified by further inclusion of about 0.54 grams of L-histidine.

The foregoing composition is prepared for intravenous administration by first dissolving the sodium salt of phenylpyruvic acid in 50 ml of distilled water with the aid of warming, and then adding the remaining components of the mixture to the resulting solution. Solution of all the substances being thus accomplished, the solution is sterilized by Millipore filtration, and tested for sterility and pyrogenicity. The solution is frozen until use. When used, the solution is thawed to room temperature and diluted to 250 ml. with sterile, pyrogen-free water.

The isotonic solution thereby resulting has a neutral pH and is satisfactory for intravenous use. The solution is stable for at least six hours at room temperature. Intravenous administration of the solution may be accomplished over a three to four hour period in a bottle protected by aluminum foil from light. In certain situations, more than one infusion may be given daily.

It will be observed that the respective quantities of the components in the mixture as set out in Table II are based on using as keto analogs at least one and a half to three times by weight the equivalent quantities of the branched chain amino acids (of valine, leucine and isoleucine) as compared to the quantities of the keto acid analogs of phenylalanine and methionine (corresponding to about two to three times on an equivalent molar basis).

In an experimental clinical program, keto analogs of five of the essential amino acids (valine, leucine, isoleucine, methionine and phenylalanine) were given parenterally or orally in varying proportions to eleven patients with portal-systemic encephalopathy and hyperammonemia. These studies were undertaken to determine the metabolism and clinical effect of these alpha-keto analogs in patients having the indicated hepatic disorders. The experiments showed that the administered keto analogs are aminated in the body. They further established that the administered mixtures of these keto acids and other essential amino acids can provide a complete source of essential amino acids without increasing blood ammonia. On the other hand, amino acids alone, administered intravenously, may lead to aggravation of symptoms in such patients. Details of the foregoing investigations are reported by Maddrey, W. C. et al. (1976) in *Gastroenterology*.

The following compositions were employed in the program:

Table III

| Substance | Quantities (gms) | | |
| --- | --- | --- | --- |
|  | A | B | C |
| Sodium alpha-keto-isovalerate | 0.96 | 3.00 | 1.44 |
| Sodium alpha-keto-isocaproate | 1.29 | 2.00 | 1.94 |
| Sodium alpha-keto-beta-methylvalerate | 0.88 | 2.40 | 1.31 |
| Sodium-alpha-keto-gamma-methyl thiobutyrate | 1.27 | 0.60 | 1.90 |
| Sodium phenylpyruvate | 1.25 | 0.80 | 1.88 |
| L-threonine | 0.50 | 0.20 | 0.50 |
| L-tryptophan | 0.25 | 0.07 | 0.25 |
| L-histidine | 0.54 | 0.00 | 0.54 |
| L-lysine hydrochloride | 0.80 | 0.20 | 0.80 |
| L-arginine | 0.00 | 1.00 | 0.00 |

The solutions for intravenous administration were prepared as described above.

For oral administration, the branched-chain keto-analogs were given in three to four times greater quantities than in Solution A; the other keto-analogs were given in 1.5 times the amounts in Solution A. All were administered as calcium salts. In addition, patients on oral treatment received small amounts of the other essential amino acids. All of these compounds were placed in gelatin capsules and given in three divided daily doses.

These selected eleven patients showed evidence of cirrhosis on liver biopsy. Nine of these had alcoholic cirrhosis; one had postnecrotic cirrhosis secondary to chronic active hepatitis; and one had cirrhosis related to inflammatory bowel disease. All eleven exhibited hyperammonemia and encephalopathy, despite potassium repletion, bowel cleansing, dietary protein restriction to less than 40 g/day, and oral neomycin (4–8 g/day) except for two patients who did not receive the drug because of an allergy in one and azotemia in another. These therapeutic measures had been instituted at least three days before the present studies and were continued throughout the period of observation. In all five patients in whom nitrogen balance studies were performed, neomycin therapy had been employed for greater than two weeks before initiation of the study. Patients were excluded who showed evidence of acute hepatitis, gastrointestinal hemorrhage, or infection.

All patients were evaluated before and after a course of therapy (one to five daily infusions) by accepted mental and neurological criteria; a few patients were also monitored neuro-psychologically during control and therapy periods.

Fasting values of arterial plasma amino acids in eleven patients are summarized in Table IV, as well as results of analysis of venous plasma in a series of 22 normal individuals. As shown in the table, the branched-chain amino acids (valine, leucine and isoleucine), taurine, lysine, histidine and alanine were significantly reduced in the patients. The reduction in alanine may be more apparent than real, because arterial plasma contains considerably less alanine than venous plasma. Arteriovenous differences for other amino acids (other than glutamine) are generally minor. Aspartate, glycine, methionine and tyrosine concentrations were significantly elevated. These abnormalities are similar to those that have been reported previously in such patients. The ratio of nine essential to eleven non-essential amino acids (excluding glutamine and glutamate) average 0.50 + 0.06 in the patients and 0.82 ± 0.03 in the normal subjects (p < 0.02). This ratio, according to several published reports, declines during protein depletion in man. In previous studies of patients with portal-systemic encephalopathy as well as in our patients, this ratio is seen to be reduced because the diminution in branched-chain amino acids and the increases in glycine and tyrosine outweigh the lesser increases in methionine, phenylalanine, or lysine observed in some reports.

amino acids. With Solution C, the concentration of isoleucine increased more than that of alloisoleucine.

The increase in alloisoleucine concentration almost certainly indicates racemization of the keto-analog of isoleucine. Although pure S (+) -alpha-keto-beta-methylvaleric acid was used in most cases, it is probable that rapid enolization and racemization of this compound took place in vivo.

In most patients, plasma amino acids were also measured two to four hours after the end of the infusion. In general, plasma amino acid composition had returned to control values, with the exception of alloisoleucine and phenylalanine, which remained elevated.

When measured the morning after the infusion, fasting plasma amino acid concentrations in most cases were not significantly different from pre-infusion values. However, alloisoleucine remained minimally elevated and phenylalanine was still slightly increased. The ratio of essential amino acids to non-essential amino acids, calculated from plasma analysis, averaged 0.50 ±0.06 ($n = 9$) before treatment and increased by +0.040 ± 0.019 the morning after therapy, a change of borderline statistical significance. The ratio increased by +.06 ± 0.02 ($p < .01$) as compared with initial values at the end of a course of therapy (one to five days).

Total plasma ketoacid concentration was measured before and after infusions on four occasions. Control concentrations averaged 0.29 mM (attributable chiefly to pyruvate and alpha-ketoglutarate). Mean increment at the end of the infusion was +0.15 mM ($n = 4$). By two to four hours after the infusion, keto-acid concentration had returned to the control value (0.28mM). Thus rapid utilization of the infused keto-analogs evidently took place.

The only plasma amino acid other than those corresponding to the infused ketoacids that changed significantly immediately after the infusions was tyrosine, which fell towards normal. Two to four hours post-infusion, there were significant decreases in the concentrations of glycine and tyrosine.

Whole blood glutamine was 469 ± 20 μM ($n = 13$) in control samples, a value not different from normal. Immediately after infusion, glutamine fell by −112 ±50 50 μM ($n = 6$), a change of borderline statistical significance (0.1 22 $p > .05$). Two to four hours after infusion, glutamine had decreased by −195 ± 48 μM or 42% ($n = 8$, $p < .01$). Whole blood glutamate remained constant.

Control ammonia N averaged 242 ± 10 μg/dl ($n = 20$) (normal = < 150 μg/dl). Immediately after the Table IV

| Plasma amino acids in portal-systemic encephalopathy* | | | | | | | | | | |
|---|---|---|---|---|---|---|---|---|---|---|
| | Tau | Asp | Thr | Ser | Pro | Cit | Gly | Ala | Val | Arg |
| Normals (22) | 73 | 15 | 200 | 139 | 206 | 43 | 262 | 401 | 267 | 103 |
| | ±6 | ±1 | ±16 | ±14 | ±14 | ±2 | ±10 | ±23 | ±8 | ±7 |
| PSE (11) | 40# | 54** | 179 | 121 | 190 | 42 | 327 | 249 | 99 | 102 |
| | ±6 | ±15 | ±22 | ±10 | ±14 | ±6 | ±22 | ±20 | ±7 | ±13 |
| | Cys | Met | Ale | Ile | Leu | Tyr | Phe | Orn | Lys | His |
| Normals (22) | 113 | 31 | 4.0 | 72 | 143 | 71 | 69 | 72 | 201 | 62 |
| | ±4 | ±0.2 | ±0.2 | ±2 | ±5 | ±2 | ±4 | ±4 | ±7 | ±2 |
| PSI (11) | 120 | 40*** | 5.8 | 39# | 64# | 95*** | 62 | 56 | 149# | 52# |
| | ±12 | ±2 | ±1.3 | ±2 | ±3 | ±10 | ±4 | ±8 | ±11 | ±3 |

*Abbreviations used in this table: Tau, taurine; asp, aspartate; Thr, theorine, Ser, serine; Pro, proline; Cit, citrulline; Gly, glycine, Ala, alanine, Val, valine; Arg, arginine; Cys, cystine; Met, methionine; Ale, alloisoleucine; Ile, isoleucine; Leu, leucine; Tyr, tyrosine; Phe, phenylalanine; Orn, arnithine; Lys. lysine; his, histidine.
significantly less than controls ($p < .01$)
**significantly greater than controls ($p < .02$)
***significantly greater than controls ($p < .01$)

Analysis of the patient's plasma was carried out before and immediately after infusion of solutions A, B and C. In two instances, a solution containing only the branched-chain keto acids was given to a single patient which led to prompt increases solely in the corresponding branched-chain amino acids.

Following infusion of Solution A, there were increases in plasma valine, leucine, phenylalanine and methionine. Isoleucine concentration increased in only one patient, but alloisoleucine increased in all. Solution B increased valine, alloisoleucine, phenylalanine and methionine, but isoleucine increased in only two of five infusions and there was no consistent increase in leucine concentration. Solution C caused significant and consistent increases in the concentrations of all six of these infusion, there was no change (242 ± 12 µg/dl, n = 14). Two to four hours later, there was again no significant change (−19 ± 14 µg/dl, n = 18). Following a course of one to five daily infusions, arterial ammonia N concentrations were slightly but significantly reduced. The mean decrement was −20 ± 9 µg/dl ($p < .05$). No difference could be discerned between the three solutions and that of the solution using only the keto acid branched-chain analogs, with respect to their effects on arterial ammonia N. Serum urea nitrogen was measured before and after courses of infusions and did not change.

Electroencephalograms before and after courses of infusion were obtained in five patients and read blindly. In three, discernible improvement from pretreatment studies occurred with the remaining two unchanged. Eight of the eleven patients were clinically improved following a course of infusions (one to five days) as judged by mental and neurological status. The remaining three patients were unchanged.

Three patients received courses of oral ketoacid therapy with corresponding control periods. Serum urea nitrogen measured throughout both control and treatment periods did not change more than 3 mg/dl in any study. Such changes were within the laboratory variation of the measurement and in no instance could account for $> 0.1$ g N per day. One patient was studied in detail over 33 days. The arterial ammonia concentration fell in both keto-analog treatment periods, and the patient was clinically improved at the end of each keto-analog treatment period as compared to the corresponding control period. The second control period was shortened because of apparent clinical deterioration with confusion. Three electroencephalograms performed during the 7 days of control period I were similar and showed excessive slow wave activity characteristic of PSE. In treatment period I, two EEG's were obtained and by the end of the 12 day period were within normal limits. In control period II (8 days), EEG abnormalities of slow wave activity reappeared and in treatment period II, the EEG again returned to normal. A standard neuropsychological battery of tests was administered during the first control period and after the end of the second treatment period. Verbal IQ increased from 88 to 100 and performance IQ from 82 to 102. Full scale IQ increased from 85 to 100 and memory function improved from low average (92) to high average (106). Nitrogen balance studies revealed improvement during both treatment periods as compared to controls.

Fasting arterial amino acids were determined in five studies on three patients who received oral ketoacids for periods ranging from 5 to 12 days. When pretreatment levels are compared to those obtained on the morning after the last day of therapy, only alloisoleucine (+20 µM ± 5 S.E.M., $p < .02$) remained elevated. Alanine alone showed a significant fall during therapy (−31 ± 11 µM, $p < .05$).

The ratio of seven essential to nine non-essential amino acids (excluding glutamine, glutamate, and also serine and threonine because of incomplete separation in some of these chromatograms) showed a rise towards normal.

Based on an analysis of the observed results, it appears that the five keto analogs administered may exert effects in portalsystemic encephalopathy that are not entirely explicable in terms of amination and utilization of the resulting amino acids. Glutamine may serve as the principal source of nitrogen for the conversion of the keto analogs to essential amino acids in portal-systemic encephalopathy. The principal nitrogen donor in muscle for converting these keto acids to amino acids has not been identified, although alanine fell in some perfusions.

It has been assumed that utilization of keto analogs for protein synthesis would require a large supply of non-protein nitrogen in the form of ammonia derived from intestinal urease action. However, measurements of urea breakdown in chronic renal failure have failed to support this view. Since nine of our eleven patients were receiving oral neomycin, intestinal breakdown of urea was probably suppressed. Despite a possible decrease in portal ammonia from this source, amination of these keto-acids was able to proceed.

Both glycine and tyrosine concentrations returned towards normal during keto-acid infusion. Elevation in these two amino acids are characteristic of portal-systemic encephalopathy. Whether the decreased observed following keto-acids represents conversion by transamination reaction to the corresponding keto-acids (glyoxylate and para-hydroxy-phenylpyruvate) remains to be established. An additional possible explanation for such decreases would be prevention of efflux of glycine and tyrosine by the increases in branched-chain amino acids resulting from keto-acid administration.

In our subjects, phenylalanine was not abnormally elevated, although others have found it to be so. Since methionine is regularly found to be increased in portal-systemic encephalopathy, an argument can be made that the keto-analogs of methionine should not be used. We have instead acted on the premise that a complete mix of essential amino acids would be necessary in order to promote protein synthesis.

In the experiments above reported, the quantities of keto-acid analogs were small relative to the total daily intake of amino acids and their carbon skeletons. At this dosage, these compounds are clearly non-toxic and do have the capacity to provide a nitrogenfree source of the essential amino acids.

Keto-acid Therapy of Congenital Hyperammonemia

Congenital disorders caused by defects in each of the five enzymes of the Krebs-Henseleit urea cycle have been previously described in the literature. The clinical and biochemical manifestations differ somewhat among these syndromes, but all are characterized by hyperammonemia, impaired mental and physical development, and episodes of vomiting, lethargy, and coma after the ingestion of protein. Hyperammonemia is most pronounced in patients with defects of the first two enzymes of this cycle: carbamyl phosphate synthetase and ornithine transcarbamylase.

Treatment of these disorders is unsatisfactory, and most children die in infancy. Protein restriction ameliorates symptoms but does not restore the ammonia concentration of plasma to normal and may prevent adequate growth.

In an article reported by the present applicant and his associates appearing in Batshaw, M. et al. (1975) *New England Journal Of Medicine*, 292:1085, a case is reported of a thirteen year old girl with a carbamyl phosphate synthetase deficiency treated with alphaketo analogs of five essential amino acids: valine, leucine, isoleucine, methionine and phenylalanine. This approach was attempted because of previous observations made in the cases of adults with hyperammonemia and portal-systemic encephalopathy caused by cirrhosis of the liver. It was reasoned that these five keto analogs of the essential amino acids might become incorporated into protein and thereby promote growth and reduce hyperammonemia because of transamination to the corresponding amino acids.

The results indicated that after intravenous infusion of the keto analogs administered the corresponding plasma amino acids, including alloisoleucine and tyrosine, rose sharply. Twenty-four hours later, fasting plasma ammonia had fallen from the pre-infusion value of 0.050 to 0.028mM. Protein intake was kept at 0.5 g/kg for two weeks. Addition of keto acids by mouth reduced plasma ammonia and alanine to normal or near normal levels. Seizures and episodes of vomiting and lethargy decreased in frequency. Urinary nitrogen decreased, suggesting that nitrogen balance improved. These data indicated that keto acids could be useful in the treatment of congenital hyperammonemia.

During the course of the treatment, numerous adjustments in the composition of the mixture were made. Eventually, normal levels of plasma ammonia and most amino acids were achieved, with three exceptions: slightly increased glutamine, pronounced alloisoleucinemia and persistently low phenylalanine. Alloisoleucine was shown not to be incorporated into plasma protein and not to be excreted in the urine; hence this abnormality was viewed as being clinically insignificant. Compared to the pretreatment period, her clinical status improved markedly. Temporary withdrawal of the supplements led to prompt increases in plasma ammonia, glutamine and alanine. From these observations, we concluded that this therapy provided safe and effective long-term management for this patient's disorder and would be useful in other cases of congenital hyperammonemia.

This patient was subsequently studied over a longer period of intermittent therapy using analogs of the essential amino acid supplemented with the essential amino acids as such under moderate protein restriction.

Whereas in the earlier treatment, only the keto analogs of the five essential amino acids were administered, in the present study various combinations of the keto analogs with and without supplemented amino acids were employed. In certain of these compositions, the hydroxy analog of the amino acid of methionine was substituted for the corresponding keto analog. Various compositions employed are shown in Table V.

mixture similar in composition to that earlier employed was administered. As before, plasma ammonia again fell, though not to normal. Withdrawal of this supplement was again followed by a rise in plasma ammonia. Resumption of similar therapy (mixtures G and H) failed to reduce plasma ammonia. At this point, it became apparent that plasma lysine, histidine and arginine had fallen to subnormal levels evidently due to inadequate N intake.

Subsequently, these amino acids plus threonine and tryptophan were added to the mixes (I through Q). At the same time, protein intake was reduced to 0.75 gm/kg per day. Over the next three weeks, plasma ammonia fell to normal concurrent with the restoration of normal or nearly normal plasma levels of lysine, histidine and arginine.

Alterations in the composition of the nutritional supplement were made chiefly in response to abnormalities in levels of amino acids and ammonia in plasma. Late in the study, histidine was noted to be still subnormal and the amount of this amino acid was increased (mixture Q).

One of the keto analogs which was frequently changed was isoleucine (mixtures H, J, K and P). We were initially concerned about plasma levels of alloisoleucine which were as high or higher than that of isoleucine. The appearance of alloisoleucine reflects racemization of alpha-keto-beta-methylvaleric acid (the keto analog of isoleucine) with subsequent transamination to yield both isoleucine and alloisoleucine. To evaluate the possibility that alloisoleucine was being incorporated into protein, plasma was obtained after six months of therapy and protein was precipitated, washed and hydrolyzed to its constituent amino acids. Plasma protein from a healthy adult was used as control. The ratios of alloisoleucine to isoleucine were 0.022 and 0.020, respectively. Pure isoleucine, when subjected to the same hydrolysis conditions, also yielded 2% alloisoleucine.

These results indicated that alloisoleucine was not incorporated into protein, and hence we continued to attempt to normalize plasma isoleucine without regard to the concentration of alloisoleucine.

Upon observation that there was subnormal levels of arginine, the quantity of this component was increased (mixture O). Plasma alanine fell, but there was little change in glutamine or ammonia. In mixture P, modest

TABLE V

| Mix | Analogues (gm of Ca or Na salt) | | | | | L-Amino Acids (gm) | | | | | |
|---|---|---|---|---|---|---|---|---|---|---|---|
|  | val | leu | ile | phe | met | phe | his | try | lys HCl | arg HCl | thr |
| G | 1.44* | 1.94* | 1.46* | 4.00* | 2.12* | 0 | 0 | 0 | 0 | 0 | 0 |
| H | 1.44* | 1.94* | 1.32* | 4.00* | 2.12# | 0 | 0 | 0 | 0 | 0 | 0 |
| I | 1.44* | 1.94* | 1.32* | 4.00* | 2.12# | 0 | 0.22 | 0.125 | 0.81 | 0.66 | 0.48 |
| J | 1.44* | 1.94* | 0.66* | 4.00* | 2.12# | 0 | 0.22 | 0.125 | 0.81 | 0.66 | 0.48 |
| K | 1.44* | 1.94* | 1.32* | 4.00* | 2.12# | 0 | 0.22 | 0.125 | 0.81 | 0 | 0.48 |
| L | 1.44* | 1.94* | 1.32* | 4.00* | 2.12# | 0 | 0.22 | 0.125 | 081 | 0.66 | 0.48 |
| M | 1.44* | 1.94* | 1.32* | 0 | 2.12# | 1.65 | 0.22 | 0.125 | 0.81 | 0.66 | 0.48 |
| N | 1.44* | 1.94* | 1.32* | 4.00** | 2.12# | 0 | 0.22 | 0.125 | 0.81 | 0.66 | 0.48 |
| O | 1.44* | 1.94* | 1.32* | 4.00** | 2.12# | 0 | 0.22 | 0.125 | 0.81 | 1.36 | 0.48 |
| P | 1.44* | 1.94* | 1.00* | 4.00** | 2.12# | 0 | 0.22 | 0.125 | 0.81 | 1.00 | 0.48 |
| Q | 1.44* | 1.94* | 1.00* | 4.00** | 2.12# | 0 | 0.33 | 0.125 | 0.81 | 1.36 | 0.48 |

*Calcium salt of keto-analogue
**Sodium salt of keto-analogue
Calcium salt of hydroxy-analogue Approximately 10 grams of the five analogs and three grams of amino acids were given three times a day as a powder or in gelatin capsules with meals. All nine (or ten) constituents of the mixture were contained in each dose. Protein intake was restricted to either 1.0 or 0.75 gm/kg per day. Following a control period, a keto acid reductions were made in both the isoleucine analog and arginine dosage. At the same time, the caloric intake was increased by adding a high carbohydrate beverage. These changes resulted in improvement in ammonia, glutamine and alanine. Histidine dosage was increased in mixture P as we have heretofore noted. In subsequent stages of the treatment during a three months period of therapy, ammonia and alanine were at the range of normal and glutamine near normal.

As a result of the treatment, significant development in the patient's psychological and physical condition were noted. The child appeared to be more alert and more responsive to her environment. She continued to increase in height at the same rate as before therapy despite protein restriction. There was also some weight gain especially during the latter part of the treatment. Nitrogen intake was higher during the treatment period owing to the nitrogen content of the added essential amino acids and the increased number of gelatin capsules consumed. Despite the increase in nitrogen intake, there was no change in the urinary nitrogen output. The additional nitrogen, 0.8 gm/day appeared to have been wholly retained. These data suggest that nitrogen balance improved.

In the previous study, when keto acids alone were first administered, there was a fall in plasma levels of arginine (the synthesis of which is perhaps limited in this child) and of those essential amino acids not supplied as keto analogs. This was associated with a rise of ammonia to abnormal levels. We inferred that protein synthesis had become limited by deficiencies of these essential amino acids and that increased blood ammonia reflected decreased utilization of the administered keto acids. Subsequently when these other essential amino acids and arginine were added to the mixture, there was a prompt rise in the respective blood amino acids and a progressive fall in ammonia to nearly normal levels.

During therapy, we found no evidence of nausea, vomiting, diarrhea, lethargy or acidosis.

The effectiveness of nutritional supplements with keto and hydroxy acids and essential amino acids was substantiated by withdrawal of these from the patient, which led to a prompt rise in ammonia, glutamine and alanine to abnormal levels. These returned towards normal when the nutritional supplements were reinstituted. Indirect evidence based on nitrogen intake and urinary nitrogen output shows increased retention of nitrogen on keto acid therapy, suggesting improved nitrogen balance. This information is supported by urinary partition of nitrogen which shows no increase in urea excretion despite an increased nitrogen intake on therapy.

In addition to this nitrogen-sparing effect, there is some evidence that the keto acids have led to improved protein tolerance. We have been able to increase the patient's nitrogen intake from 2.8 gm/day used in our initial study to 4.6 gm/day without losing positive nitrogen balance or precipitating hyperammonemia. We have observed no essential difference in attained results whether the hydroxy analog or the keto analog of methionine was employed.

The mixtures reported in Table V contained a high proportion of the keto or hydroxy analog of phenylalanine. The comparatively high proportion of either of these compounds is not generally required but was used in this instance because the patient had a peculiar defect in the metabolism of this amino acid. Mixtures recommended for more general use in the treatment of congenital hyperammonemia are set out below.

Another type of congenital hepatic disorder attributed to inborn error in amino acid metabolism is cetrullinemia, in which there is a deficiency in argininosuccinic acid synthetase in the liver. In this condition, there is manifested an excessive amount of citrulline in blood, urine and cerebrospinal fluid, and ammonia intoxication. In a number of previous reported cases of lethal neonatal citrullinemia death ensued at a mean age of 5.2 days.

A 20 day old infant diagnosed as suffering from neonatal citrullinemia showed a plasma citrulline of 67.7 mg%. Intravenous infusion of a mixture of the alpha keto analogs of valine, leucine, isoleucine, phenylalanine and methionine, produced a 2-fold (leucine) to a 24-fold (methionine) increase in the corresponding amino acids, thus demonstrating effective transamination.

The infant was then placed on oral administration of a mixture of the alpha keto analogs of the first four of the above-named amino acids and the alpha hydroxy analog of methionine, supplemented with prepared formula and lipid to a total of 120 cal/kg/day. Blood ammonia declined from initial values between 412 and 943 $\mu g\%$ to 44 $\mu g\%$ and citrulline was reduced to 14.2mg%. Weight gain was established and all abnormal neurological signs resolved. At 45 days, the patient's clinical and biochemical condition showed marked improvement, indicating the use of these analogs of essential amino acids to be an effective mode of therapy in this condition.

In general, for the effective treatment of congenital hyperammonemia in children, the dosages tabulated below are recommended for intravenous administration:

|  | grams |
| --- | --- |
| Keto-valine | 0.9 (Na or Ca salt) |
| Keto-leucine | 1.2 (Na or Ca salt) |
| Keto-isoleucine | 0.8 (Na or Ca salt) |
| Keto or hydroxy methionine | 1.2 (Na or Ca salt) |
| Phenylpyruvate or lactate | 1.2 (Na or Ca salt) |
| Histidine | 0.2 |
| Threonine | 0.2 |
| Tryptophan | 0.1 |
| Lysine hydrochloride | 0.3 |
| Arginine hydrochloride | 2.0 |

The foregoing mixture can be intravenously administered in a period of 3 to 4 hours in a newborn infant of normal body weight (6 to 7 pounds; ~2.7 to 3.2 kgs).

For oral usage in congenital hyperammonemia in infants of about such weight, the recommended daily dosage is:

|  | grams |
| --- | --- |
| Keto-valine | 0.68 (Na or Ca salt) |
| Keto-leucine | 0.94 (Na or CA salt) |
| Keto-isoleucine | 0.69 (Na or Ca salt) |
| L-phenyl lactate or |  |
| Phenylpyruvate | 0.47 (Na or Ca salt) |
| Keto or hydroxy methionine | 0.50 (Na or Ca salt) |
| Lysine hydrochloride | 0.20 |
| Histidine | 0.12 |
| Threonine | 0.15 |
| Tryptophan | 0.10 |
| Arginine hydrochloride | 1.0 |

The dosage for oral administration, it will be observed, is considerably smaller than that indicated above for intravenous use, because the latter is generally employed in emergency situations while oral ingestion is utilized for maintenance therapy in long term growth and usually in conjunction with some dietary protein.

The foregoing dosages, as indicated, are intended for infants. For larger children, the oral and intravenous doses are increased with relation to their height and weight (surface area). These mixtures are recommended for use in children with defects in any of the five known urea cycle enzyme defects with the exception of that due to arginase deficiency. In the latter condition, arginine accumulates in the plasma, so that arginine is excluded from the mixture. In some instances, effective treatment is obtained by oral or intravenous administration of only the calcium salts of the keto analogs of the branched chain amino acids.

The keto acid analogs described herein are known substances. Although methods of preparing compounds of this type are well known, a relatively inexpensive method comprises reaction of diethyloxalate with the ethylester of the next lowest homologous organic acid (of the desired keto acid) in the presence of sodium methoxide and subsequently hydrolizing the resulting product to yield the keto acid. Hydroxy acid analog is conveniently prepared by reacting the corresponding amino acid with nitrous acid.

What is claimed is:

1. A composition for improving nitrogen balance in patients having hepatic disorders comprising a mixture in form for oral or parenteral administration to adults suffering from such disorders, said composition consisting essentially of the components in the following approximate proportions by weight:

| | |
|---|---|
| 0.0 to 3.0 grams | phenylpyruvic acid; sodium or calcium salt |
| 4.0 to 8.0 grams | alpha-ketoisovaleric acid; sodium or calcium salt |
| 3.0 to 5.0 grams | alpha ketoisocaproic acid; sodium or calcium salt |
| 0.0 to 3.0 grams | alpha-keto-gamma-methylthiobutyric acid; sodium or calcium salt |
| 2.0 to 4.0 grams | alpha-keto-beta-methylvaleric acid; sodium or calcium salt |
| ~0 to 0.1 gram | L-tryptophan |
| ~0 to 0.4 gram | L-threonine |
| ~0 to 0.4 gram | L-lysine monohydrochloride |
| 1.0 to 4.0 grams | L-arginine. |

2. A composition as defined in claim 1 which further includes about 0.54 grams L-histidine.

3. A composition as defined in claim 2 in form for parenteral administration, said composition being in form of a sterilized isotonic aqueous solution.

4. A method for improving nitrogen balance in patients having hepatic disorders which method comprises oral or parenteral administration in effective dosages to subjects on a low protein diet of a composition comprising a mixture of the keto analogs of the branched-chain essential amino acids valine, leucine and isoleucine, each of said recited keto analogs being present in effective quantity.

5. A method for improving nitrogen balance in patients having hepatic disorders which comprises oral or parenteral administration in effective dosage to a subject on a diet of small amounts of protein, a therapeutic composition consisting essentially of the components in the following ranges of proportions by weight:

| | |
|---|---|
| 0.0 to 2.0 parts | phenylpyruvic acid; calcium salt |
| 4.0 to 8.0 parts | alpha-ketoisovaleric acid; calcium salt |
| 3.0 to 5.0 parts | alpha ketoisocaproic acid; calcium salt |
| 0.0 to 3.0 parts | alpha-keto-gamma-methylthiobutyric acid; calcium salt |
| 2.0 to 4.0 parts | alpha-keto-beta-methylvaleric acid; calcium salt |
| ~0 to 0.1 parts | L-tryptophan |
| ~0 to 0.4 parts | L-threonine |
| ~0 to 0.4 parts | L-lysine monohydrochloride |
| 1.0 to 4.0 parts | L-arginine |

6. A method as defined in claim 5 wherein said composition further includes about 0.54 parts L-histidine.

7. A method as defined in claim 6 in form for parenteral administration, said composition being in form of a sterilized isotonic aqueous solution.

8. The method as defined in claim 5 wherein said composition is orally administered.

9. A method for treatment of hyperammonemia which comprises oral or parenteral administration in effective dosages to subjects on a low protein diet of a composition comprising a mixture of the keto analogs of the essential amino acids valine, phenylalanine, methionine, leucine and isoleucine, each of said recited keto analogs being present in effective quantity, said keto analogs being present in the form of the alpha-keto acids per se or salts of the alpha-keto acids.

10. The method as defined in claim 9 wherein each of the recited analogs is in the form of its calcium or sodium salt.

11. A method as defined in claim 10 wherein said composition also contains in effective quantities in amino acid form: L-arginine, L-lysine hydrochloride, L-threonine and L-tryptophan.

12. A method as defined in claim 11 wherein said composition further contains in effective quantity L-histidine.

13. A method as defined in claim 10 wherein the five recited keto acid analogs are present in said composition in amounts to afford dosages constituting at least the minimum daily requirement of the corresponding essential amino acid.

14. A method as defined in claim 10 wherein the quantities of the keto acids of valine, leucine and isoleucine are each present in said composition in approximately one and a half to three times by weight that of phenylalanine and methionine.

15. A method as defined in claim 9 wherein histidine is also present in said composition in effective quantity in the form of its alpha keto acid analog.

16. A method as defined in claim 9 wherein the five recited keto analogs are present as salts in the weight proportions: 4 to 8 parts valine analog, 3 to 5 parts leucine analog, 2 to 4 parts isoleucine analog, 0.0 to 3.0 parts of methionine analog and 0 to 3 parts phenylalanine analog.

17. A method as defined in claim 16 wherein said composition is parenterally administered as a sterilized isotonic aqueous solution.

18. A method for treatment of congenital hyperammonemia in children having deficiency of enzymes of the Krebs-Henseleit urea cycle, which method comprises oral or parenteral administration to such patient in effective dosage of a therapeutic composition comprising a mixture of the keto analogs of the essential amino acids valine, phenylalanine, methionine, leucine and isoleucine, each of said recited keto analogs being present in effective quantity, said keto analogs being present in the form of the alpha-keto acids per se or salts of the alpha-keto acids.

19. A method as defined in claim 18 wherein the administration composition also contains in effective quantities in amino acid form: L-arginine, L-lysine hydrochloride, L-threonine, and L-tryptophan.

20. A method as defined in claim 19 wherein the administration composition further contains in effective quantity L-histidine.

21. A method as defined in claim 18 wherein the composition is intravenously administered and consists essentially of the following components in proportions by weight:

| | |
|---|---|
| sodium or calcium alpha-keto-isovalerate | 0.9 |
| sodium or calcium alpha-keto-isocaproate | 1.2 |
| sodium or calcium alpha-keto-beta-methylvalerate | 0.8 |
| sodium or calcium phenylpyruvate | 1.2 |
| sodium or calcium alpha-keto-gamma-methyl thiobutyrate | 1.2 |
| L-arginine hydrochloride | 2.0 |
| L-histidine | 0.2 |
| L-tryptophan | 0.1 |
| L-lysine hydrochloride | 0.3 |
| L-threonine | 0.2 |

22. A method as defined in claim 18 wherein the composition is orally administered and consists essentially of the following components in proportions by weight:

| | |
|---|---|
| sodium or calcium alpha-keto-isovalerate | 0.68 |
| sodium or calcium alpha-keto-isocaproate | 0.94 |
| sodium or calcium alpha-keto-beta-methylvalerate | 0.69 |
| sodium or calcium phenylpyruvate | 0.47 |
| sodium or calcium alpha-keto-gamma-methylthiobutyrate | 0.50 |
| lysine hydrochloride | 0.20 |
| histidine | 0.12 |
| threonine | 0.15 |
| tryptophan | 0.10 |
| arginine hydrochloride | 1.0 |

23. The method as defined in claim 18 wherein the composition is intravenously administered to patients having a deficiency in arginase, and consists essentially of the following components in proportions by weight:

| | |
|---|---|
| sodium or calcium alpha-keto-isovalerate | 0.9 |
| sodium or calcium alpha-keto-isocaproate | 1.2 |
| sodium or calcium alpha-keto-beta-methylvalerate | 0.8 |
| sodium or calcium phenylpyruvate | 1.2 |
| sodium or calcium-alpha-keto-gamma-methylthiobutyrate | 1.2 |
| L-histidine | 0.2 |
| L-tryptophan | 0.1 |
| L-lysine hydroclhoride | 0.3 |
| L-threonine | 0.2 |

24. The method as defined in claim 18 wherein the composition is orally administered to patients having a deficiency in arginase, and consists essentially of the following components in proportions by weight:

| | |
|---|---|
| sodium or calcium alpha-keto-isovalerate | 0.68 |
| sodium or calcium alpha-keto-isocaproate | 0.94 |
| sodium or calcium alpha-keto-beta-methylvalerate | 0.69 |
| sodium or calcium phenylpyruvate | 0.47 |
| sodium or calcium alpha-keto-gamma-methylthiobutyrate | 0.50 |
| lysine hydrochloride | 0.20 |
| histidine | 0.12 |
| threonine | 0.15 |
| tryptophan | 1.0 |

25. A method for treatment of congenital hyperammonemia in children having deficiency of enzymes of the Krebs-Henseleit urea cycle, which method comprises oral or parenteral administration to such patient in effective dosage a therapeutic composition comprising the calcium salts of the keto analogs of valine, leucine and isoleucine.

* * * * *